US00PP18954P3

(12) United States Plant Patent
Jennings

(10) Patent No.: US PP18,954 P3
(45) Date of Patent: Jun. 17, 2008

(54) RASPBERRY PLANT NAMED 'JOAN J'

(50) Latin Name: *Rubus idaeus*
Varietal Denomination: Joan J

(75) Inventor: Derek L. Jennings, Maidstone (GB)

(73) Assignee: Medway Fruits, Maidstone, Kent (GB)

( * ) Notice: Subject to any disclaimer, the term of this patent is extended or adjusted under 35 U.S.C. 154(b) by 207 days.

(21) Appl. No.: 11/305,154

(22) Filed: Dec. 19, 2005

(65) Prior Publication Data

US 2007/0143891 P1 Jun. 21, 2007

(51) Int. Cl.
*A01H 5/00* (2006.01)

(52) U.S. Cl. ..... Plt./204
(58) Field of Classification Search ..... Plt./204
See application file for complete search history.

(56) References Cited

U.S. PATENT DOCUMENTS

2007/0143891 P1 * 6/2007 Jennings ..... Plt./204

OTHER PUBLICATIONS

UPOV ROM GTITM Computer Database, GTI Jouve Retrieval Software 2007/01 Citations for 'jOAN j'.*

Jennings, D. L. Breeding pirmocane–fruiting raspberries at Medway Fruits—Progress and prospects. Proceedings of the Eigth Internation *Rubus* and Ribes Symposium, Invergowrie, Dundee, UR, Jul. 4–12, 2001, vol. 1. Acta Horticulturae (585): p. 85–89 (2001).*

* cited by examiner

*Primary Examiner*—Wendy C. Haas
(74) *Attorney, Agent, or Firm*—Buchanan Ingersoll & Rooney PC

(57) ABSTRACT

A new and distinct *Rubus idaeus* L. plant is provided that is the product of a controlled breeding program. The new Raspberry plant abundantly forms attractive glossy very large conical-shaped medium red mature fruit of excellent flavor that is longer than broad in configuration. Numerous relatively stout spine-free canes are formed. An early-primocane cropping season is displayed that commonly begins on about July 25$^{th}$ and continues to about September 15$^{th}$ at Maidstone, Kent, United Kingdom. The berries are amenable for consumption as a high grade fresh fruit.

1 Drawing Sheet

Botanical/commercial classification: *Rubus idaeus*/Raspberry Plant.

Varietal denomination: cv. Joan J.

SUMMARY OF THE INVENTION

The instant plant (i.e., *Rubus idaeus* L.) was created in the course of a planned breeding program carried out at Maidstone, Kent, United Kingdom. Two parents were crossed in the hope that they would contribute the desired characteristics. The female parent (i.e., the seed parent) was the 'Joan Squire' cultivar (non-patented in the United States) and the subject of European Plant Breeders Rights Grant No. 5680. The 'Joan Squire' cultivar is a cross between two hybrids of complex origin. The male parent (i.e., the pollen parent) was the 'Terri-Louise' cultivar (non-patented in the United States). The parentage of the new cultivar can be summarized as follows:

'Joan Squire'×'Teri-Louise'.

The seeds resulting from the above pollination were sown and small plants were obtained which were physically and biologically different from each other. Selective study resulted in the identification of a single plant of the new cultivar.

It was found that the new Raspberry plant of the present invention possesses the following combination of characteristics:

(a) displays a vigorous and erect growth habit, (b) displays an early-primocane fruiting characteristic and commonly begins fruiting in early August at Maidstone, Kent, United Kingdom, (c) forms attractive glossy very large conical-shaped medium red mature fruit with excellent flavor that is longer than broad in configuration, (d) displays numerous relatively stout spine-free canes, and (e) is well suited for consumption as high grade fresh fruit.

The new cultivar well meets the needs of the berry industry. The earliness of fruiting, large fruit size and excellent eating qualities make the new cultivar an ideal choice for amateur growers and pick-your-own growers.

The new cultivar of the present invention can be readily distinguished from its parental cultivars. More specifically, 'Joan Squire' cultivar displays a semi-erect growth habit, commonly forms canes having a lesser thickness, and forms lighter colored pale red fruit that begins to crop later during mid-August. The 'Terri-Louise' cultivar forms spiny canes unlike the new cultivar of the present invention.

The new cultivar also can be readily distinguished from the 'Joan Irene' cultivar (U.S. Plant Pat. No. 17,986) since the new cultivar commonly flowers and fruits approximately four weeks earlier.

The new cultivar has been found to undergo asexual propagation at Maidstone, Kent, United Kingdom by in vitro tissue culture and by the rooting of cuttings. Asexual propagation by the above-mentioned methods as performed at such location has shown that the characteristics of the new cultivar are strictly transmissible from one generation to another. Accordingly, the new variety undergoes asexual propagation in a true to type manner.

The new cultivar initially was designated MF93118/5, and subsequently has been named 'Joan J'.

BRIEF DESCRIPTION OF THE PHOTOGRAPH

The accompanying photograph shows as nearly true as is reasonably possible to make the same in a color illustration of this character a typical specimen of the new cultivar. The photograph was obtained on Aug. 19, 1998 at Maidstone, Kent, United Kingdom. The illustrated plant had been asexually reproduced by the rooting of a cutting that was planted during 1997. The upright growth habit and attractive fruit in various stages of maturity are illustrated.

DETAILED DESCRIPTION

The description is based on the observation of specimens of the new cultivar growing at Maidstone, Kent, United Kingdom. Observations of plant growth were made while growing under plastic and the fruit was observed under field growing conditions. The plants had been asexually reproduced by the rooting of cuttings. Color references is made to The R.H.S. Colour Chart of The Royal Horticultural Society, London, England.

Botanical classification: *Rubus idaeus* L.

Plant: Displays a tall, vigorous and erect growth habit. The canes are relatively numerous, stout, spine-free and commonly are thicker than those of the 'Joan Squire' parental cultivar. A medium number of young shoots commonly is displayed. The canes commonly display little or no branching. New canes commonly display a slight bloom. The internode lengths at mid-cane typically measure approximately 60 mm. The leaves commonly bear three or five leaflets. Young shoots and the leaf petioles commonly are near Yellow-Green Group 145B in coloration. The tips of young shoots commonly do not bear anthocyanin coloration. Petioles typically measure approximately 55 to 60 mm in length. The leaves commonly are relatively flat and display three or five leaflets. Terminal leaflets commonly are approximately 95 mm in length and approximately 70 mm in width. In cross section the leaves display little or no tendency to assume a concave configuration. The upper surfaces of mature leaves are near Green Group 137B in coloration, and the under surfaces of mature leaves are near Green Group 138B in coloration.

Flowering: Begins early on current season's canes. The flowering time is close to that of the 'Autumn Bliss' Cultivar (U.S. Plant Pat. No. 6,597). In the south of England flowering commonly begins about June 24$^{th}$ and continues to about July 25$^{th}$.

Bearing type: Fruit is mainly borne on the current season's canes. The time of fruit ripening on a current season's cane is early and commonly begins about July 25$^{th}$ and continues to about September 15th at Maidstone, Kent, United Kingdom. This can be compared to a first ripening time of mid-August for the 'Joan Squire' parental cultivar at the same location. The start of ripening is similar to that of the 'Autumn Bliss' cultivar at the same location. The new cultivar has not been assessed for double cropping.

Fruit: Attractive very large conical-shaped fruit is formed that is longer than broad. Typical yields are approximately 20 percent greater than those of 'Autumn Bliss' cultivar primarily reflecting an increase of fruit weight of approximately the same magnitude. The earliest formed fruits during the first three weeks of the season commonly weigh approximately 6 grams on average and the fruits formed during the second three weeks of the season commonly weigh approximately 4 grams on average to provide an overall fruit weight of approximately 5 grams throughout the season. The fruit color is an attractive glossy medium red at full maturity that is near Red Group 58B in coloration. The coloration further darkens when the fruit is over-ripe. The fruit flavor is excellent. The attractive fruits tend to readily separate from the receptacle and commonly measure approximately 30 mm in length and approximately 25 mm in width at the widest point. The pedicels are near Yellow-Green Group 145B in coloration.

Resistance to pests and diseases: During observations to date the new cultivar of the present invention has displayed adequate resistance to all pests and diseases encountered at Maidstone, Kent, United Kingdom.

Market: The berries are suitable for consumption as a high grade fresh fruit and also are amenable to processing.

I claim:

1. A new and distinct cultivar of Raspberry plant having the following combination of characteristics:

(a) displays a vigorous and erect growth habit, (b) displays an early-primocane fruiting characteristic and commonly beings fruiting on about July 25$^{th}$ at Maidstone, Kent, United Kingdom, (c) forms attractive glossy very large conical-shaped medium red mature fruit with excellent flavor that is longer than broad in configuration, (d) displays numerous relatively stout spine-free canes, and (e) is well suited for consumption as high grade fresh fruit;

substantially as illustrated and described.

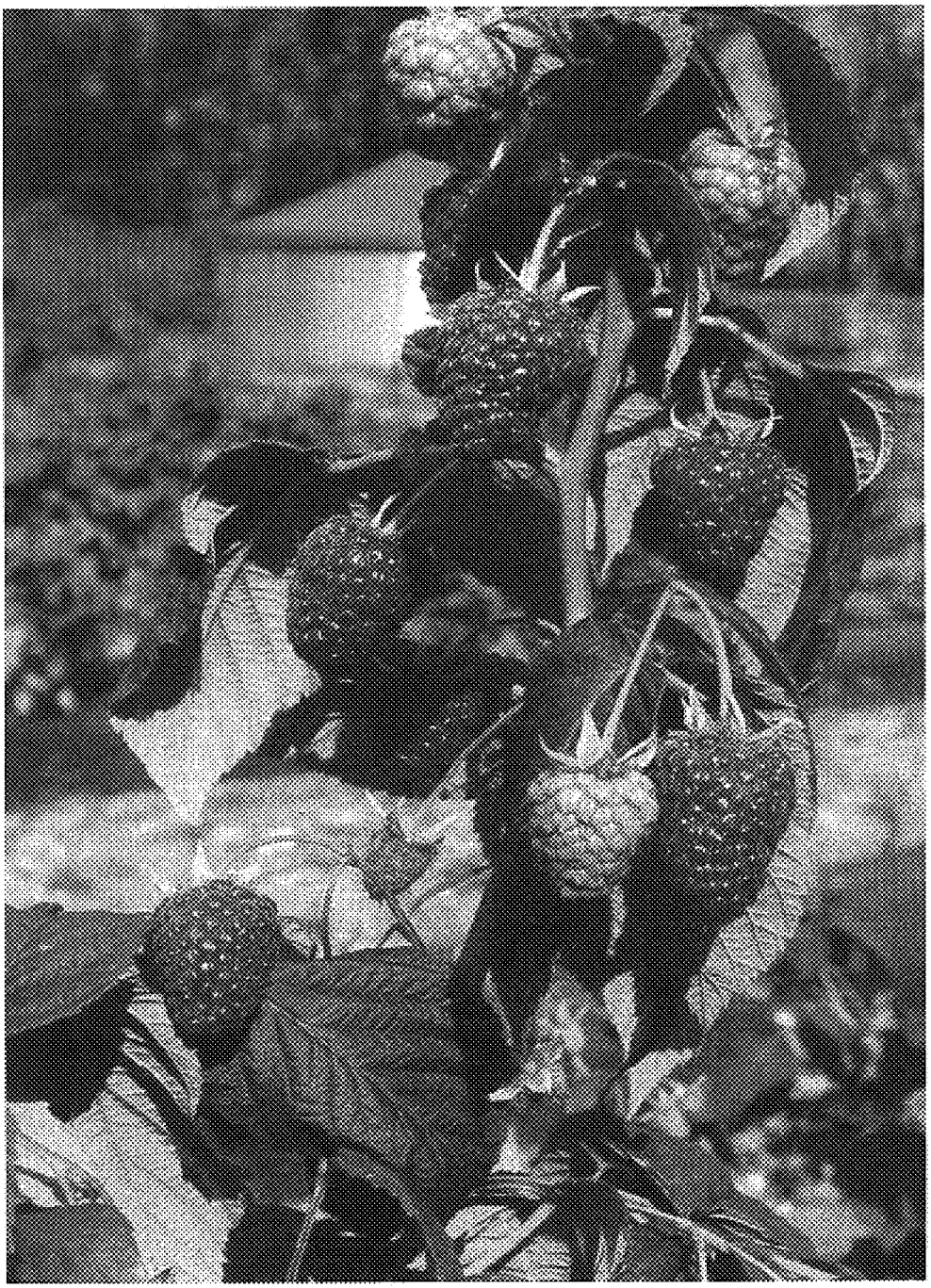

* * * * *